United States Patent [19]

Harris

[11] Patent Number: 5,519,143
[45] Date of Patent: May 21, 1996

[54] PROCESS FOR THE ISOLATION AND PURIFICATION OF AN IMIDAZOLE STEREOISOMER FROM A MIXTURE OF STEREOISOMERS BY SELECTIVE PRECIPITATION

[75] Inventor: Gregory D. Harris, Wilmington, Del.

[73] Assignee: The Du Pont Merck Pharmaceutical Company, Wilmington, Del.

[21] Appl. No.: 360,248

[22] Filed: Sep. 19, 1994

[51] Int. Cl.$^6$ .................. C07D 233/68; C07D 233/90; C07D 233/66; C07D 401/10
[52] U.S. Cl. .................. 548/253; 548/333.5; 548/334.5; 548/312.1
[58] Field of Search .................. 548/253, 333.5

[56] References Cited

U.S. PATENT DOCUMENTS

| 4,340,598 | 7/1982 | Furukawa et al. | 548/339.5 X |
| 4,772,723 | 9/1988 | Frazer et al. | 548/334.5 |
| 5,254,546 | 10/1993 | Ardecky et al. | 514/381 |

FOREIGN PATENT DOCUMENTS

| 2354786 | 2/1973 | Germany | 548/334.5 |

Primary Examiner—Floyd D. Higel

[57] ABSTRACT

A method for the isolation and purification of an imidazole compound, useful as an angiotensin II receptor inhibitor compound or as a key intermediate therefor, from a mixture of it with its regioisomer in a solvent by treament of the mixture with a strong acid to effect selective precipitation of the desired regioisomeric imidazole salt.

11 Claims, No Drawings

PROCESS FOR THE ISOLATION AND PURIFICATION OF AN IMIDAZOLE STEREOISOMER FROM A MIXTURE OF STEREOISOMERS BY SELECTIVE PRECIPITATION

FIELD OF THE INVENTION

This invention relates to a method for the isolation and purification of imidazole compounds useful as angiotensin II receptor inhibitor compounds or as key intermediates therefor.

BACKGROUND OF THE INVENTION

Regioselective alkylation of polysubstituted imidazoles is of importance especially with regard to Angiotensin II antagonists. The mechanisms of selective alkylation are somewhat understood and can be used in some circumstances to control reaction products, i.e. the distribution of N-alkylated regioisomeric products. However, no generally applicable methods currently exist for the regioselective alkylation of these important imidazoles in quantitative yield. The product by prior art methods is usually a mixture of regioisomers as shown in Scheme 1.

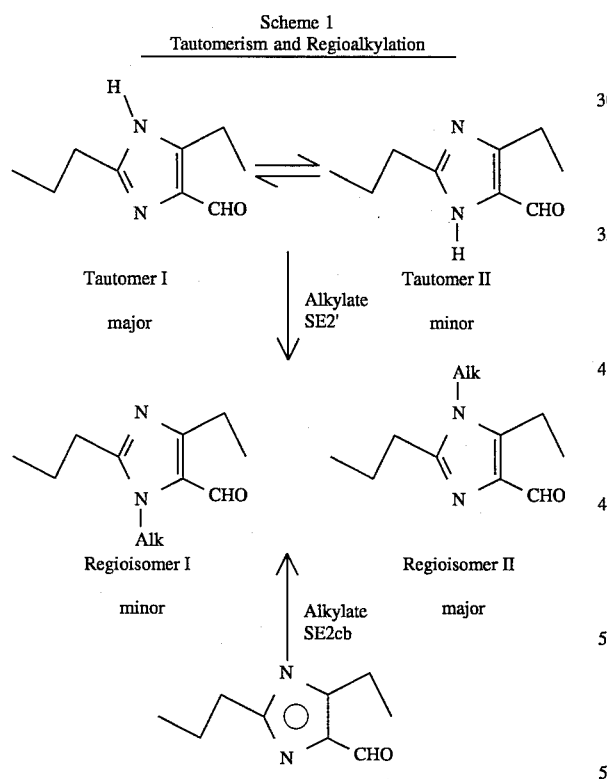

German Patent DE 2354786, Galenika Pharm Chem Ind., describes a nitration of an alkylimidazole to form the same general class of compounds as in the present invention. The isomers are separated by pH control so that the stronger base is protonated and stays in solution and the weaker, presumably non protonated, base is precipitated. The stronger base is isolated at pH 9. The desired N-alkylated imidazole is not isolated by salt formation/crystallization.

It is apparent, as determined by the nonquantitative formation of either regioisomer during N-alkylation, and the lack of suitable methods for the large scale purification of N-alkylated imidazoles that a method of purifying these very important compounds to obtain pure products from alkylation is needed when suitable crystallization is not an option because of the physical form, e.g. when product mixture is an oil

SUMMARY OF THE INVENTION

This invention relates to methods for the isolation and purification of N-alkylated substituted imidazoles of the formula (I) from a mixture of compounds of the formula (I) and (II)

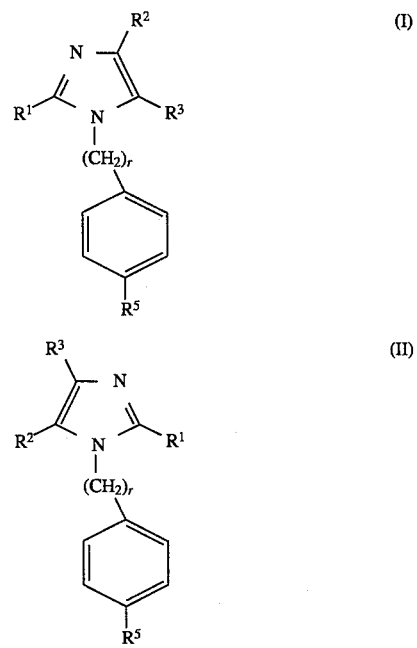

wherein:

$R^1$ is selected from H; C1–C6 alkyl, C1–C6 fluoroalkyl, C2–C10 alkenyl, or C2–C10 alkynyl each optionally substituted by —$CO_2$—(C1–C6 alkyl); C4–C10 cycloalkylalkyl, C3–C6 cycloalkyl, C5–C10 cycloalkylalkenyl, or C5–C10 cycloalkylalkynyl each optionally substituted by 1–13 —F or 1–3 —$CO_2$—(C1–C6 alkyl); phenyl, naphthyl, or aryl-(C 1–C4 alkyl) optionally substituted with —F or —$CO_2$—(C1–C6 alkyl); —$(CH_2)_s$O $(CH_2)_m$R5 optionally substituted with —F or —$CO_2$—(C1–C6 alkyl); benzyl optionally substituted with up to 2 groups selected from halo, C1C–4 alkoxy, $NO_2$, or C1–C4 alkyl;

$R^2$ is C1–C6 alkyl, C2–C6 alkenyl, C2–C6 alkynyl, phenyl-(C1–C6)alkyl, phenyl-(C1–C6)alkenyl, (C1–C6)alkoxy-(C1–C6)alkyl, hydroxy-(C1–C6)alkyl, hydroxy-(C2–C6)alkenyl, hydroxy-(C2–C6)alkynyl, aminocarbonylalkyl, carbonylaminoalkyl, halogen;

$R^3$ is —CHO, —$COR^1$, —$CO_2H$, —$CO_2R^1$, —CN, —$CONHR^1$, —$NO_2$, or C1–C6 fluoroalkyl;

$R^5$ is H, Br, I, F, $CF_3$, (C1–C4) alkyl, —$CO_2$-alkyl, —$C(CF_3)_2OH$, —$NHSO_2CH_3$, —C(=O)NHNHSO$_2$CF$_3$,

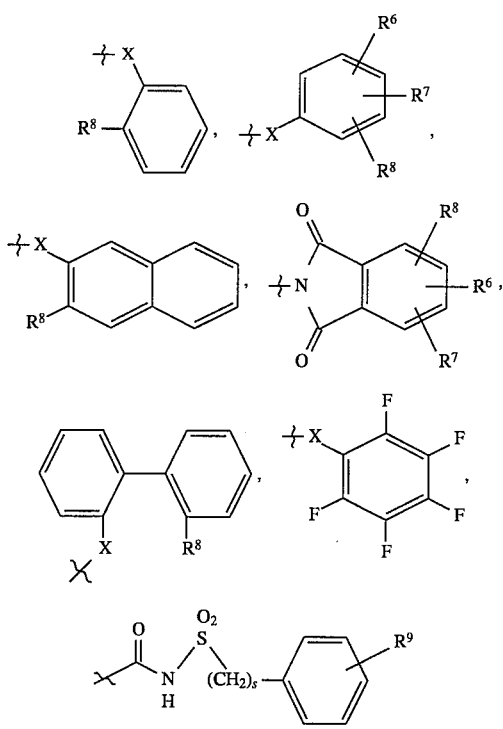

or aryl optionally substituted by $R^9$;

$R^6$ is H, halo, $NO_2$, CN, C1–C4 alkyl, C1–C4 alkoxy, C1–C4 acyloxy, —$NHSO_2CH_3$, —$NHSO_2CF_3$, —CONHO—(C1–C4) alkyl, tetrazolyl, trityl protected tetrazolyl, or furyl;

$R^7$ is H, halo, C1–C4 alkyl, or C1–C4 alkoxy;

X is a single bond, —CO—, —CH2—, —O—, —CONH—, —NHCO—, —OCH$_2$—, —CH$_2$O—, —NHSO$_2$—, —SO$_2$NH—, —CH=CH—, —CF=CH—, —CH=CF—, —CF=CF—, —CH$_2$CH$_2$—, —CF$_2$CF$_2$—, or

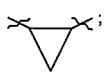

;

$R^8$ is independently selected at each occurrence from: H, —NHSO$_2$CH$_3$, —NHSO$_2$CF$_3$, —NHCOCF$_3$, or —CONHNHSO$_2$CF$_3$;

$R^9$ is H, C1–C4 alkyl, or phenyl;

r is independently 0 to 2;

m is independently 1 to 5;

s is independently 0 to 5;

said method comprising the step of:
contacting a mixture of a compound of the formula (I) and its regioisomer of formula (II) (in a mole ratio of 50–99:50–1; (I):(II)) in a solvent such as ethyl acetate, methyl acetate, isopropyl acetate, n-butyl acetate, methylene chloride, methyl t-butyl ketone, tetrahydrofuran, lower alcohols, methyl isobutyl ketone, water, or mixtures thereof, with 0.5–2.0 molar equivalents of a strong acid, such as toluene-4-sulfonic acid, methane sulfonic acid, hydrochloric acid, phosphoric acid, sulfuric acid, hydrobromic acid, triflic acid, or trifluoro acetic acid, to form the acid salt of a compound of the formula (I), and then separating the solids and liquid such as by filtration, centrifugation or other methods known to the skilled artisan.

A preferred method of this invention is a method for the isolation and purification of N-alkylated substituted imidazoles of the formula (I) from a mixture of compounds of formulae (I) and (II) wherein:

$R^1$ is H, C1–C10 alkyl, C2–C10 alkenyl, or C2–C10 alkynyl;

$R^2$ is C1–C6 alkyl, C2–C6 alkenyl, or C2–C6 alkynyl;

$R^3$ is —CHO or —CO$_2R^1$;

$R^5$ is Br, I, F, CF$_3$, —NHSO$_2$CH$_3$, CH$_3$,

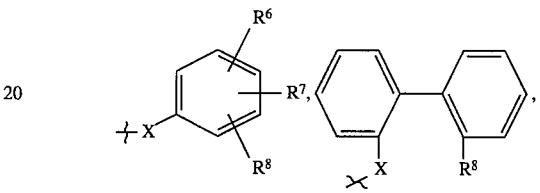

or phenyl or naphthyl optionally substituted by $R^9$;

$R^6$ is H, tetrazolyl, or trityl protected tetrazolyl;

$R^8$ is H;

and wherein the substituents $R^7$, $R^9$, X and r are as defined above.

A specifically preferred method of this invention is a method for the isolation and purification of the following compounds from their regioisomers of formula (II):

N-(4-bromobenzyl)-2-propyl-4-ethyl-5-formyl imidazole;

N-(4-bromobenzyl)-2-propyl-4-ethyl-5-carboxymethyl-imidazole;

N-(4-bromobenzyl)-2-propyl-4-ethyl-5-carboxy-imidazole;

N-[4-(0-(trityltetrazole)phenyl)benzyl]-4-ethyl-5-formyl-2-propyl-imidazole;

N-[4-(0-(trityltetrazole)phenyl)benzyl]-5-carboxymethyl-4-ethyl-2-propyl-imidazole; and N-[4-(0-(trityltetrazole)phenyl)benzyl]-5-carboxy-4-ethyl-2-propyl-imidazole.

The present invention may be generally understood according to Scheme 2.

Scheme 2

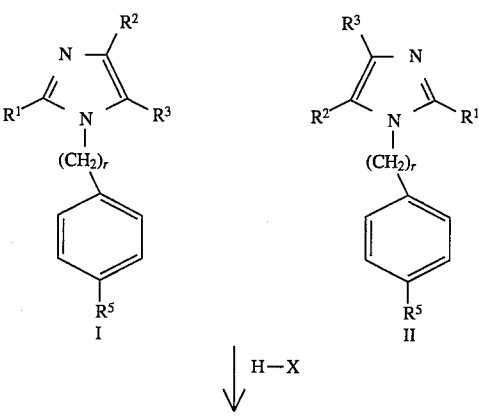

-continued
Scheme 2

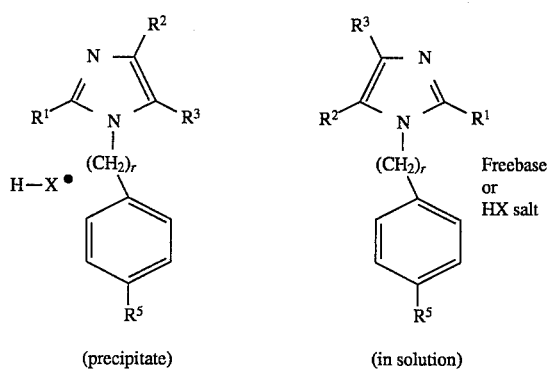

(precipitate)　　　　　(in solution)

Separation of isomeric mixtures is facilitated because of physical property differences between their salts which is exploited. This technique offers significant advantages for large scale manufacture since it avoids chromatographic purification, as well as undesired oily or poorly crystalline solid products.

DETAILED DESCRIPTION OF THE INVENTION

This invention provides a novel method for the isolation and purification of compounds of the formula (I) from a mixture of compounds of the formula (I) and (II) which are useful as intermediates in the preparation of Angiotensin II antagonists. In the present invention, an N-alkylated imidazole of formula (I) is obtained in the regioisomerically pure salt form from a mixture of N-alkylated free base regioisomers of formula (I) and (II).

In this process, a mixture of regioisomers (mole ratio ~50–99:50–1), compounds of the formula (I) and (II) are treated with at least 0.5–2.0 molar equivalents of a strong acid to preferentially form the salt of compound of the formula (I) which is then isolated by separation of solids and liquid. The mixture of compounds of the formula (I) and (II) in a solvent, such as ethyl acetate, methyl acetate isopropyl acetate, n-butyl acetate, methylene chloride, methyl t-butyl ketone, tetrahydrofuran, lower alcohols, methyl isobutyl ketone, water, or mixtures thereof, is treated with at least with 0.5–2.0 molar equivalents of a strong acid, such as toluene-4-sulfonic acid, phosphoric acid, sulfuric acid, methane sulfonic acid, hydrochloric acid, hydrobromic acid, triflic acid, or trifluoro acetic acid, to form the crystalline acid salt of a compound of the formula (I). The desired salt is separated from the free base or salt of compound of the formula (II) in solution by separation of the solids and liquid such as by filtration, centrifugation or other methods known to the skilled artisan.

The present invention may be better understood according to scheme 3.

Scheme 3

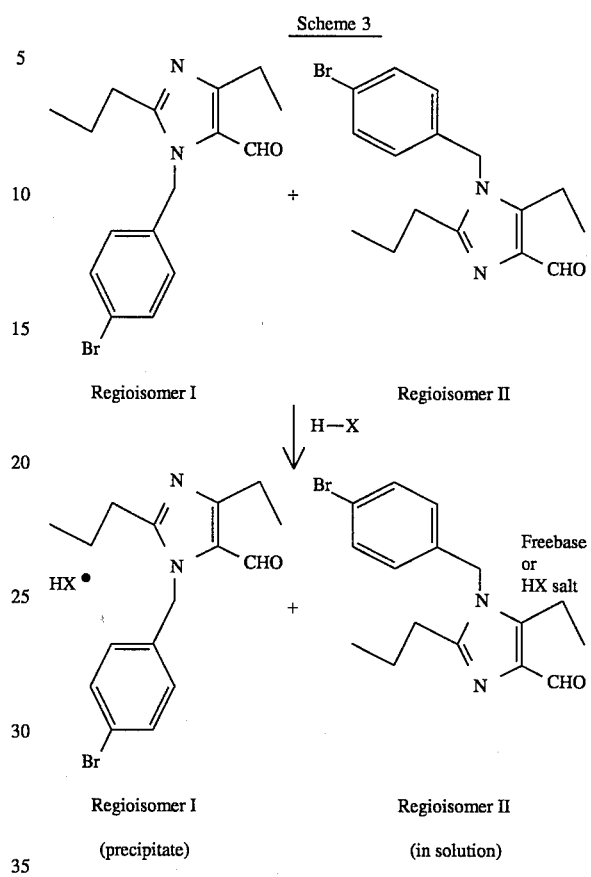

Regioisomer I　　　　　Regioisomer II

Regioisomer I　　　　　Regioisomer II
(precipitate)　　　　　(in solution)

The salt formation of the present invention is carried out in suitable solvents which may be readily selected by one of skill in the art of organic synthesis, said suitable solvents generally being any solvent which is substantially nonreactive with the starting materials (reactants), the intermediates, or products.

The preferred solvent system is ethyl acetate, methyl isobutyl ketone, water, n-butyl acetate or mixtures thereof.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

When any variable (for example, $R^1$, $R^2$, $R^3$, $R^5$, m, etc.) occurs more than one time in any constituent or formula for a compound, its definition on each occurrence is independent of its definition at every other occurrence. Thus, for example, if a group is shown to be substituted with 0–3 $R^6$, then said group may optionally be substituted with up to three $R^6$ and $R^6$ at each occurrence is selected independently from the defined list of possible $R^6$. Also, combinations of substituents and/or variables are permissible only if such combinations result in stable compounds. By stable compound or stable structure it is meant herein a compound that is sufficiently robust to survive isolation to a useful degree of purity from a reaction mixture. Similarly, by way of example, for the group —$C(R^6)_2$—, each of the two $R^6$ substituents on C is independently selected from the defined list of possible $R^6$.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono- or bicyclic ring systems, such as cyclopropyl, cyclobutyl, cyclopentyl, cyclohexyl, or cycloheptyl. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like.

"C4–C10 cycloalkylalkyl" is intended to mean a cycloalkyl group attached through an alkyl bridge. In a similar manner the term "C5–C10 cycloalkylalkenyl" is intended to mean a cycloalkyl group attached through an alkenyl brige, and the term "C5–C10 cycloalkylalkynyl" is intended to mean a cycloalkyl group attached through an alkynyl bridge.

As used herein, "fluoroalkyl" is intended to mean a C1–C6 straight chained or branched "alkyl" group substituted with 1 to 13 fluoro groups.

As used herein, "hydroxyalkyl" is intended to mean a C1–C6 straight chained or branched "alkyl" group substituted with 1 to 6 hydroxy groups.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; the term "arylalkyl" represents an aryl group attached through an alkyl bridge. By way of examples: the term "$C_7$–$C_{10}$ arylalkyl" is intended to refer to an aryl group attached through a $C_1$–$C_4$ alkyl bridge to the residue of the indicated compound; the term "($C_1$–$C_3$ alkyl)aryl" is intended to refer to a $C_1$–$C_3$ alkyl group which is attached through an aryl ring to the residue of the indicated compound; the term "aryl($C_1$–$C_3$ alkyl)" is intended to refer to an aryl group attached through a $C_1$–$C_3$ alkyl group to the residue of the indicated compound.

As used herein, "strong acid" is intended to mean any acid of the group consisting of: toluene-4-sulfonic acid, phosphoric acid, sulfuric acid, methane sulfonic acid, hydrochloric acid, hydrobromic acid, triflic acid, trifluoro acetic acid, or other such acids with similar acidities.

The preferred strong acid is toluene-4-sulfonic acid, hydrochloric acid or triflic acid.

The preferred molar equivalents of strong acid is 0.8 to 1.2.

When a bond to a substituent is shown to cross the bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of a given formula via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogens on the designated atom is replaced with a selection from the indicated group, provided that the designated atom's normal valency is not exceeded, and that the substitution results in a stable compound.

The scope of the present invention may be further understood, without limitation, by the following examples.

EXAMPLE 1

N-(4-bromobenzyl)-2-propyl-4-ethyl-5-formyl imidazole 2-propyl-4-ethyl-5-formyl imidazole (20 g; 0.12 moles) was dissolved in N,N dimethylacetamide (130 mL) and cooled to 0°–5° C. under an atmosphere of nitrogen. 4-Bromobenzylbromide (30.1 g; 0.127 moles) and pulverised anhydrous potassium carbonate (23.3 g; 0.169 moles) were added, and the resulting mixture was stirred and allowed to warm to 20° C. over a period of 16 hours to form a mixture of regioisomers (I:II, 80:20). Water (500 ml) and ethyl acetate (350 ml) were added. The mixture was agitated and allowed to settle and the layers separated. The organic phase was washed twice with 3% aqueous sodium chloride and then distilled at atmospheric pressure until the distillate was clear and the contents reached a temperature of 77° C. Dry ethyl acetate (135 ml) was added and the solution cooled to 25° C. Toluene-4-sulfonic acid hydrate (22.9 g; 0.12 moles) was added and almost immediately a white precipitate formed. The mixture was held at 25° C. for 5 minutes, heated to a gentle reflux for 10 minutes and finally cooled to 20° C. The precipitate was filtered, washed with ethyl acetate (50 ml) and dried to a constant weight at 50° C. in vacuo to yield N-(4 -bromobenzyl)-2-propyl-4-ethyl-5-formyl imidazole as the tosylate salt. (53.6 g; 88% yield) as a white solid. mp 158° C. NMR (CDCl$_3$) δ0.85–0.95 (t,3H), 1.35–1.50 (t,3H), 1.60–1.80 (m,2H), 2.39 (s,3H), 3.00–3.15 (m,4H), 5.60 (s,2H), 6.90–7.00 (d,2H), 7.10–7.21 (d,2H), 7.42–7,50 (d,2H), 7.75–7.82 (d,2H), 9.80 (s,1H).

EXAMPLE 1a (Alternate Solvent for Isolation of Salt)
N-(4-bromobenzyl)-2-propyl-4-ethyl-5-formyl imidazole 2-propyl-4-ethyl-5-formyl imidazole (20 g; 0.12 moles) was dissolved in N,N-dimethylacetamide (130 ml) and cooled to 0°–5° C. under an atmosphere of nitrogen. 4-Bromobenzylbromide (30.1 g; 0.127 moles) and pulverised anhydrous potassium carbonate (23.3 g; 0.169 moles) were added and the resulting mixture was stirred and allowed to warm to 20° C. over a period of 16 hours to form a mixture of regioisomers (I:II, 80:20). Water (500 ml) and methyl-isobutyl ketone (MIBK:250 ml) were added. The mixture was agitated, allowed to settle and the layers separated. The aqueous phase was further extracted with MIBK (250 ml). The combined organic phases were washed twice with 3% aqueous sodium chloride and then distilled at atmospheric pressure to remove approximately 150 ml of distillate. The clear solution was then cooled to 50° C. A solution of toluene-4-sulfonic acid hydrate (22.9 g; 0.12 moles) in MIBK (100 ml) at 50° C. was added and almost immediately a white precipitate formed. The mixture was cooled to 25° C. and held for one hour. The precipitate was filtered, washed with MIBK (50 ml) and dried to a constant weight at 50° C. in vacuo to yield N-(4-bromobenzyl)-2-propyl-4-ethyl- 5-formyl imidazole as the tosylate salt (53.6 g; 88% yield) as a white solid.

EXAMPLE 2

N-(4-bromobenzyl)-2-propyl-4-ethyl-5-carboxymethyl-imidazole 2-propyl-4-ethyl-5-carboxymethyl-imidazole (4 g; 0.02 moles) was dissolved in N,N-dimethylacetamide (26 ml) under an atmosphere of nitrogen. 4-Bromobenzylbromide (5.08 g; 0.021 moles) and anhydrous cesium carbonate (9.3 g; 0.029 moles) were added and the resulting mixture was stirred at 20° C. for 4 hours to form a mixture of regioisomers (I:II, 80:20). Water (100 ml) and n-butyl acetate (100 ml) were added. The mixture was agitated, allowed to settle and the layers separated. The organic phase was washed twice with 3% aqueous sodium chloride and then distilled under atmospheric pressure until the distillate was clear and the contents reached a temperature of 124° C. The solution was cooled to 50° C. and toluene-4-sulfonic acid hydrate (3.9 g; 0.02 moles) was added. The resulting solution was slowly cooled to 20° C. when a precipitate formed and was further cooled to 5° C. and held for 1 hour. The precipitate was filtered, washed with n-butyl acetate (5 ml) and dried to constant weight at 50° C. in vacuo to yield N-(4-bromobenzyl)-2-propyl-4-ethyl-5-carboxymethyl imidazole as the tosylate salt. (8 g; 73% yield) as a white solid. HNMR (CDCl$_3$) δ0.85–0.95 (t,3H), 1.25–1.40 (t,3H), 1.60–1.80 (m,2H), 2.38 (s,3H), 3.00–3.15 (m,4H), 3.88 (s,3H), 5.62 (s,3H), 6.88–6.95 (d,2H), 7.15–7.25 (d,2H), 7.45–7.55 (d,2H), 7.78–7.90 (d,2H).

EXAMPLE 3

N-(4-bromobenzyl)-2-propyl-4-ethyl-imidazole-5-carboxylic acid 2-propyl-4-ethyl-5-carboxymethyl-imidazole (20 g; 0.102M) was dissolved in N,N-dimethylacetamide (130 ml) under an atmosphere of nitrogen. 4-Bromobenzylbromide (25.5 g; 0.107 moles) and anhydrous pulverised potassium carbonate (19.7 g; 0.143 moles) were added and the resulting mixture was stirred at 20° C. for 48 hours to form a mixture of regioisomers (I:II, 80:20). Water (500 ml) and toluene (350 ml) were added which produced a small exotherm. The temperature was adjusted to 25° C. and the mixture allowed to settle and the layers separated. The organic phase was washed with water (150 ml) and brine (150 ml) and then distilled under reduced pressure to a volume of 100 ml. Water (1.84 g; 0.102 moles) and potassium t-butoxide in THF (1 Molar; 204 ml) were added and the mixture stirred for two hours under a nitrogen atmosphere. Water (250 ml) was added and the mixture was agitated, settled and the layers separated. The aqueous phase was washed with toluene (200 ml) and then distilled under vacuum until clear, i.e. until all remaining solvent had distilled. The aqueous solution, containing N-(4-bromobenzyl)-2-propyl-4-ethyl-imidazole- 5-carboxylic acid and N-(4-bromobenzyl)-2 -propyl-5-ethyl-imidazole-4-carboxylic acid as potassium salts in approximately 80:20 ratio, was added to a solution of concentrated hydrochloric acid (100 ml) in water (500 ml) and stirred for 15 minutes. The resulting precipitate was filtered, washed with dilute hydrochloric acid (1 Molar; 100 ml) and dried in vacuo at 50° C. to constant weight to yield N-(4-bromobenzyl)-2 -propyl-4-ethyl-imidazole-5-carboxylic acid hydrochloride salt as a white solid (34.2 g; 74% yield). HNMR (DMSO) δ0.80–0.90 (t,3H), 1.15–1.25 (t,3H), 1.48–1.68 (m,2H), 2.80–3.00 (m,4H), 5.68 (s,2H), 7.00–7.10 (d,2H), 7.50–7.60 (d, 2H).

EXAMPLE 4

N-[4-(0-(trityltetrazole)phenyl)benzyl]-4-ethyl-5-formyl-2-propyl-imidazole, tosylate salt To methyl isobutyl ketone solution (MIBK, 250 ml) containing N-[4-(0-(trityltetrazole)phenyl)benzyl]-4 -ethyl-5-formyl-2-propyl-imidazole and N-[4-(0 -(trityltetrazole)phenyl)benzyl]-5-ethyl-4-formyl-2 -propyl-imidazole, 0.11 moles in approximately 80:20 ratio (I:II), was added a solution of toluene-4-sulfonic acid hydrate (22.9 g; 0.12 moles) in MIBK (100 ml) at 50° C. Almost immediately a white precipitate formed. The mixture was cooled to 25° C. and held for one hour. The precipitate was filtered, washed with MIBK (50 ml) and dried to a constant weight at 50° C. in vacuo to yield N-[4-(0-(trityltetrazole)phenyl)benzyl]-4-ethyl- 5-formyl-2-propyl-imidazole as the tosylate salt.

What is claimed is:

1. A method for the isolation and purification of a compound of the formula (I) from a mixture of compounds of formulae (I) and (II)

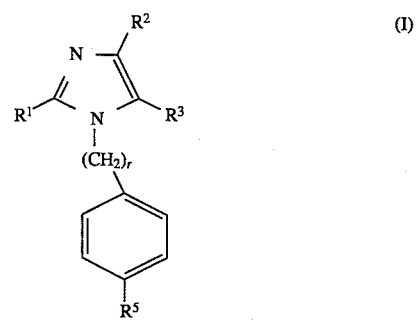

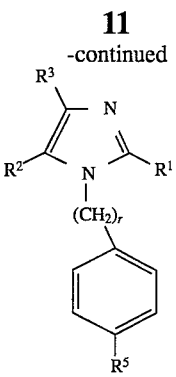

(II)

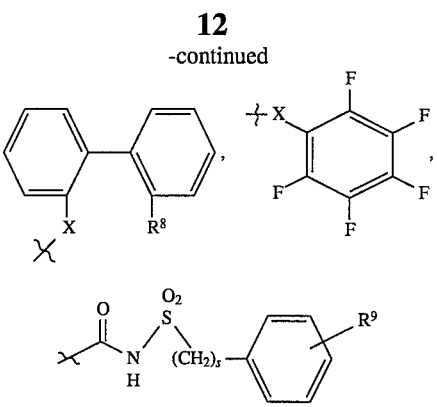

wherein:

R¹ is selected from H; C1–C6 alkyl, C1–C6 fluoroalkyl, C2–C10 alkenyl, or C2–C10 alkynyl; C1–C6 alkyl-CO₂—(C1–C6 alkyl), C1–C6 fluoroalkyl-CO₂—(C1–C6 alkyl), C2–C10 alkenyl-CO₂—(C1–C6 alkyl), or C2–C10 alkynyl-CO₂—(C1–C6 alkyl); C4–C10 cycloalkylalkyl, C3–C6 cycloalkyl, C5–C10 cycloalkylalkenyl, or C5–C10 cycloalkylalkynyl; C4–C10 cycloalkylalkyl substituted by 1–13 —F, C3–C6 cycloalkyl substituted by 1–13 —F, C5–C10 cycloalkylalkenyl substituted by 1–13 —F, or C5–C10 cycloalkylalkynyl substituted by 1–13 —F; C4–C10 cycloalkylalkyl-CO₂—(C1–C6 alkyl), C3–C6 cycloalkyl-CO₂— (C1–C6 alkyl), C5–C10 cycloalkylalkenyl-CO₂—(C1–C6 alkyl), or C5–C10 cycloalkylalkynyl-CO₂—(C1–C6 alkyl); phenyl, naphthyl, or aryl-(C1–C4 alkyl); phenyl substituted with —F, naphthyl substituted with —F, or aryl-(C1–C4 alkyl) substituted with —F; phenyl-CO₂— (C1–C6 alkyl), naphthyl-CO₂—(C1–C6 alkyl), or aryl-(C1–C4 alkyl)-CO₂—(C1–C6 alkyl); —(CH₂)ₛO(CH₂)ₘR⁵; —(CH₂)ₛO(CH₂)ₘR⁵ substituted with —F; —(CH₂)ₛO(CH₂)ₘR⁵ substituted with —CO₂—(C1–C6 alkyl); benzyl; or benzyl substituted with up to 2 groups selected from halo, C1–C4 alkoxy, NO₂, or C1–C4 alkyl;

R² is C₁–C₆ alkyl, C₂–C₆ alkenyl, C₂–C₆ alkynyl, phenyl-(C₁–C₆)alkyl, phenyl-(C₁–C₆)alkenyl, (C₁–C₆)alkoxy-(C₁–C₆)alkyl, hydroxy-(C₁–C₆)alkyl, hydroxy-(C₂–C₆)alkenyl, hydroxy-(C₂–C₆)alkynyl, aminocarbonylalkyl, carbonylaminoalkyl, halogen;

R³ is —CHO, —COR¹, —CO₂H, —CO₂R¹, —CN, —CONHR¹, —NO₂, or C1–C6 fluoroalkyl;

R⁵ is H, Br, I, F, CF₃, (C1–C4)alkyl, —CO₂-alkyl, —C(CF₃)₂OH, —NHSO₂CH₃, —C(=O)NHNHSO₂CF₃,

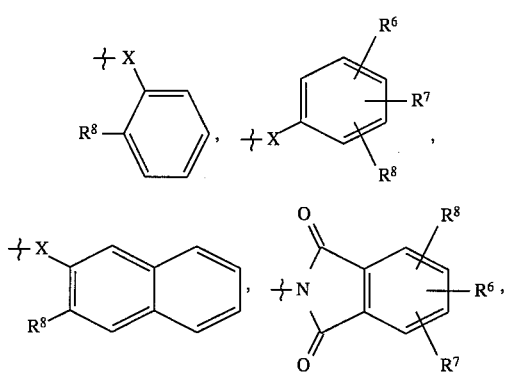

aryl; or aryl substituted by R⁹;

R⁶ is H, halo, NO₂, CN, C1–C4 alkyl, C1–C4 alkoxy, C1–C4 acyloxy, —NHSO₂CH₃, —NHSO₂CF₃, —CONHO—(C1–C4)alkyl, tetrazolyl, trityl tetrazolyl, or furyl;

R⁷ is H, halo, C1–C4 alkyl, or C1–C4 alkoxy;

X is a single bond, —CO—, —CH2—, —O—, —CONH—, —NHCO—, —OCH₂—, —CH₂O—, —NHSO₂—, —SO₂NH—, —CH=CH—, —CF=CH—, —CH=CF—, —CF=CF—, —CH₂CH₂—, —CF₂CF₂—, or

R⁸ is independently selected at each occurrence from: H, —NHSO₂CH₃, —NHSO₂CF₃, —NHCOCF₃, or —CONHNHSO₂CF₃;

R⁹ is H, C1–C4 alkyl, or phenyl;

r is independently 0 to 2;

m is independently 1 to 5; and s is independently 0 to 5;

said method comprising the step of:
treating a mixture of a compound of the formula (I) and its regioisomer of formula (II) (in a mole ratio of 50–99:50–1; (I):(II)) in a solvent selected from the group consisting of ethyl acetate, methyl acetate, isopropyl acetate, n-butyl acetate, methylene chloride, methyl t-butyl ketone, tetrahydrofuran, lower alcohols, methyl isobutyl ketone, water, or mixtures thereof, with 0.5–2.0 molar equivalents of a strong acid, selected from the group consisting of toluene-4-sulfonic acid, methane sulfonic acid, hydrochloric acid, phosphoric acid, sulfuric acid, hydrobromic acid, triflic acid, or trifluoro acetic acid, to form the acid salt of a compound of the formula (I), and then separating the solids and liquid.

2. The method of claim 1 wherein for the compounds of formulae (I) and (II):

R¹ is H, C1–C10 alkyl, C2–C10 alkenyl, or C2–C10 alkynyl;

R² is C1–C6 alkyl, C2–C6 alkenyl, or C2–C6 alkynyl;

R³ is —CHO or —CO₂R¹;

$R^5$ is Br, I, F, $CF_3$, —$NHSO_2CH_3$, $CH_3$,

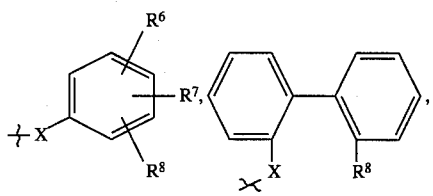

or phenyl, naphthyl, phenyl substituted by $R^9$; or naphthyl substituted by $R^9$ $R^6$ is H, tetrazolyl, or trityl tetrazolyl;

$R^8$ is H;

and wherein the substituents $R^7$, $R^9$, X and r are as defined in claim 1.

3. The method of claim 2 wherein the compound of formula (I) is N-(4-bromobenzyl)-2-propyl-4-ethyl-5-formyl imidazole.

4. The method of claim 2 wherein the compound of formula (I) is N-(4-bromobenzyl)-2-propyl-4-ethyl-5-carboxymethyl-imidazole.

5. The method of claim 2 wherein the compound of formula (I) is N-(4-bromobenzyl)-2-propyl-4-ethyl-5-carboxy-imidazole.

6. The method of claim 2 wherein the compound of formula (I) is N-[4-(0-(trityltetrazole)phenyl)benzyl]-4-ethyl-5-formyl-2-propyl-imidazole.

7. The method of claim 2 wherein the compound of formula (I) is N-[4-(0-(trityltetrazole)phenyl)benzyl]-5-carboxymethyl-4-ethyl-2-propyl-imidazole.

8. The method of claim 2 wherein the compound of formula (I) is N-[4-(0-(trityltetrazole)phenyl)benzyl]-5-carboxy-4-ethyl-2-propyl-imidazole.

9. The method of claim 1 or claim 2 wherein the solvent is ethyl acetate, methyl isobutyl ketone, water, n-butyl acetate or mixtures thereof.

10. The method of claim 9 wherein the strong acid is toluene-4-sulfonic acid, hydrochloric acid or triflic acid.

11. A method of claim 10 wherein the molar equivalents of strong acid is 0.8 to 1.2.

* * * * *